(12) United States Patent
Doets et al.

(10) Patent No.: US 11,592,363 B2
(45) Date of Patent: Feb. 28, 2023

(54) MOLTEN METAL SAMPLERS FOR HIGH AND LOW OXYGEN APPLICATIONS

(71) Applicant: HERAEUS ELECTRO-NITE INTERNATIONAL N.V., Houthalen (BE)

(72) Inventors: Jan Doets, Houthalen (BE); Guy Neyens, Houthalen (BE); Hilaire Vaes, Houthalen (BE); Frank Mingneau, Houthalen (BE); Dries Beyens, Houthalen (BE)

(73) Assignee: HERAEUS ELECTRO-NITE INTERNATIONAL N.V., Houthalen (BE)

( * ) Notice: Subject to any disclaimer, the term of this patent is extended or adjusted under 35 U.S.C. 154(b) by 0 days.

(21) Appl. No.: 16/434,901

(22) Filed: Jun. 7, 2019

(65) Prior Publication Data

US 2019/0376876 A1    Dec. 12, 2019

(30) Foreign Application Priority Data

Jun. 12, 2018    (EP) .................................... 18177317

(51) Int. Cl.
*G01N 1/12*        (2006.01)
*G01N 33/2028*    (2019.01)
(Continued)

(52) U.S. Cl.
CPC .............. *G01N 1/125* (2013.01); *F16L 9/006* (2013.01); *G01N 1/2035* (2013.01);
(Continued)

(58) Field of Classification Search
CPC .. G01N 1/125; G01N 33/2028; G01N 33/204; G01N 1/2035; G01N 2001/002; F16L 9/006
(Continued)

(56) References Cited

U.S. PATENT DOCUMENTS 3,255,634 A * 6/1966 Cavalier ................ G01N 1/125
                                                    73/864.54
3,315,529 A    4/1967 Heinrich
(Continued)

FOREIGN PATENT DOCUMENTS

EP    0095102 A1    11/1983
EP    3336511 A1    6/2018
(Continued)

OTHER PUBLICATIONS

Dulski, Thomas, "A manual for the chemical analysis of metals", Mar. 1, 1996, ASTM E1009.

*Primary Examiner* — Robert R Raevis
(74) *Attorney, Agent, or Firm* — Blank Rome LLP

(57) ABSTRACT

The present invention relates to a sampler for taking samples from a molten metal bath, particularly a molten steel bath, the sampler comprising:
a carrier tube having an immersion end;
a sample chamber assembly arranged on the immersion end of the carrier tube, the sample chamber assembly comprising a cover plate and a housing, wherein the housing comprises an immersion end having an opening;
an inflow conduit having a first end for receiving molten metal and a second end, opposite the first end, wherein the second end is in communication with the opening, wherein the opening is configured to receive the molten metal from the inflow conduit;
a measuring head, wherein the sample chamber and the second end of the inflow conduit are at least partly arranged in the measuring head; and
a de-oxidant material arranged along a central axis of the inflow conduit, wherein at least part of the de-oxidant material is arranged near the second end of the inflow conduit inside the measuring head, and wherein the inflow
(Continued)

conduit comprises first coupling means, arranged on the second end of the inflow conduit, wherein the de-oxidant material comprises second coupling means, to interact with the first coupling means on the inflow conduit to anchor the de-oxidant material in a position along the central axis of the inflow conduit. The invention also relates to a sampler for taking samples from a molten metal bath, particularly a molten steel bath, the sampler comprising:

a carrier tube having an immersion end;

a sample chamber assembly arranged on the immersion end of the carrier tube, the sample chamber assembly comprising a cover plate and a housing, wherein the housing comprises an immersion end having an opening;

an inflow conduit having a first end for receiving molten metal and a second end, opposite the first end, wherein the second end is in communication with the opening, wherein the opening is configured to receive the molten metal from the inflow conduit;

a measuring head, wherein the sample chamber and the second end of the inflow conduit are at least partly arranged in the measuring head; and a metal bushing, wherein the metal bushing coupling the inflow conduit to the sample chamber.

11 Claims, 7 Drawing Sheets

(51) Int. Cl.
| | | |
|---|---|---|
| *G01N 33/204* | (2019.01) | |
| *F16L 9/00* | (2006.01) | |
| *G01N 1/20* | (2006.01) | |
| *G01N 1/00* | (2006.01) | |

(52) U.S. Cl.
CPC ....... *G01N 33/204* (2019.01); *G01N 33/2028* (2019.01); *G01N 2001/002* (2013.01)

(58) Field of Classification Search
USPC .............. 73/863.83, 864.53, 864.55–864.59; 164/4.1; 266/99
See application file for complete search history.

(56) References Cited

U.S. PATENT DOCUMENTS

| | | | |
|---|---|---|---|
| 3,646,816 A | 3/1972 | Hance et al. | |
| 3,974,698 A | 8/1976 | Scott, Jr. | |
| 4,002,072 A | 1/1977 | Collins | |
| 4,007,641 A | 2/1977 | Kelsey | |
| 4,084,441 A * | 4/1978 | McDevitt | G01N 1/125 73/864.56 |
| 4,166,391 A * | 9/1979 | McDevitt | G01N 1/125 73/864.59 |
| 4,211,117 A | 7/1980 | Cure | |
| 4,237,734 A | 12/1980 | McDevitt | |
| 4,361,053 A * | 11/1982 | Jones | G01N 1/125 73/864.53 |
| 4,401,389 A | 8/1983 | Theuwis | |
| 4,453,424 A * | 6/1984 | Hackett | G01N 1/125 73/864.58 |
| 4,503,716 A * | 3/1985 | Wuensch | G01N 1/125 73/864.57 |
| 4,569,237 A * | 2/1986 | Cassidy | G01N 1/125 73/864.58 |
| 5,415,052 A | 5/1995 | Baerts | |
| 2016/0209342 A1* | 7/2016 | Beyens | G01K 7/025 |

FOREIGN PATENT DOCUMENTS

| | | |
|---|---|---|
| EP | 3336512 A1 | 6/2018 |
| EP | 3336513 A1 | 6/2018 |
| EP | 3336514 A1 | 6/2018 |
| FR | 2282633 A2 | 3/1976 |
| GB | 1456353 A | 11/1976 |
| JP | H0674949 A | 3/1994 |
| JP | 2007121093 A | 5/2007 |
| TW | I399252 B | 6/2013 |
| TW | I460035 B | 11/2014 |

* cited by examiner

MOLTEN METAL SAMPLERS FOR HIGH AND LOW OXYGEN APPLICATIONS

CROSS REFERENCE TO RELATED APPLICATION

This application claims the benefit of Europe Application No. 18177317.7, filed Jun. 12, 2018, the entire contents of which are incorporated by reference herein.

FIELD OF THE INVENTION

The invention relates to samplers for taking samples from a molten metal bath, particularly a molten steel bath, both in high and low oxygen applications.

BACKGROUND OF THE INVENTION

During the processing of metals in their molten state, it is necessary to obtain a representative sample of the molten metal at various stages of the process, for example, for the analysis or evaluation of either the chemical composition or the metallographic structure of the metal sample. Different methods for analyzing molten metals during manufacturing and further processing are known in the art.

Historically, the composition of a solidified metal sample is often determined using arc spark-optical emission spectroscopy, Spark-OES, equipment. Spark-OES involves exciting atoms of a target sample of which knowledge of the composition is desired, and examining the wavelength of photons emitted by atoms during transition from an excited state to a lower energy state. Each element in the periodic table emits a characteristic set of discrete wavelengths when its atoms return from an excited state to a lower energy state. By detecting and analyzing these wavelengths, the elemental composition of a sample can be determined in accordance with a calibration curve, thereby showing the relationship between the spectral intensity ratio (i.e. absolute radiation power of an element/absolute radiation power of the base metal) and the concentration of the element in the standard sample.

In order to lay flat upon the analysis opening of the spectrometer, the metal sample cannot have any extensions and the analysis surface of the metal sample must be smooth. There can be no part of the sample or sample housing which will break the plane of the analysis surface. The sample must span the analysis opening of the spectrometer and be of sufficient flatness to facilitate inert gas purging of the spark chamber and present a contiguous sample surface toward the anode.

The procedures and processes to obtain a representative analysis of metals are well known in the art as described in In Dulski, T. R. A Manual for the Chemical Analysis of Metals, ASTM International, 1996. Until know, it has been generally believed that the metal sample and the instrumentation used for its analysis are independent of each other and, as such, one does not influence the other.

Conventional sampling devices which provide a coupon or disc of solid metal for use in spectrographic analysis are known. The geometric shape and dimensions of the solidified metal coupons obtained by such sampling devices will sometimes be specific to the type of metal or metallographic need. A general category of samples that are obtained by immersion devices for Spark-OES analysis are samples having a disc or oval shape and a diameter or long length of 28 to 40 mm. Most commonly, such samples have a diameter or long length of about 32 mm and a thickness of 4 to 12 mm. Some samplers, commonly known as lollipop samplers, may produce a differently shape sample, ranging from round to oval or longer, according to the requirements of the user, but most samples still have a diameter or long length of about 32 mm. Other samplers, commonly known as dual thickness samplers, combine two thicknesses within the same sample.

Typical sampling devices designed to obtain samples of molten metal for analysis by Spark-OES include a sample chamber or mold cavity configured to be filled with molten metal upon immersion of the sampling device into the molten metal bath. The molds which delineate the mold cavity or sampling chamber are typically either a two-part clam shell type arrangement or a ring covered on its upper and lower sides by flat plates. Once the sample of metal is solidified, the molds are discarded and the sample is transported to the Spark-OES for analysis.

U.S. Pat. No. 3,646,816 describes this type of expendable immersion sampler, in which both flat surfaces of a disc-like sample are formed by chill-plates to achieve more rapid freezing and a pair of smoother surfaces which require less clean-up prior to analysis. Other prior art patents, such as U.S. Pat. No. 4,211,117, relate to a similar concept, while U.S. Pat. Nos. 4,401,389 and 5,415,052 provide examples of this metallurgical sample being combined with other sensors, one of which could be a temperature measuring sensor.

Samples produced by conventional sampling devices have a diameter of about 32 mm in a direction parallel to the spectrometer opening and a thickness of 4 to 12 mm in a direction perpendicular to the spectrometer opening. It has been found that a solidified sample of conventional thicknesses requires surface grinding from 0.8 to 5 mm of the as-cast surface, in order to achieve an analysis surface which is free from metal and non-metallic segregation. Conventional samples can only achieve this surface state after preparation processes to produce a geometry that is typically at least 28 mm in diameter in a direction parallel to the spectrometer opening and has a thickness which is typically less than 12 mm in a direction perpendicular to the opening. This after-preparation geometry is often handled by pre-analysis preparation equipment that mechanically grinds the sample surface and is also convenient for handling by robotic manipulators which advance the sample from preparation through analysis and removal to await the next sample.

Eliminating the need for surface preparation shortens the analysis time and is economically favorable to the metal producer. Various solutions to this problem are described in EP3336513A1, EP3336514A1, EP3336512A1, and EP3336511A1. These documents relate to Direct Analysis, DA, samplers which are a newly developed type of molten metal immersion sampler, which produce DA samples. DA samples do not require any kind of surface preparation before being analyzed, and thus can result in significant economic benefit both in terms of the availability of timely chemistry results as well as laboratory time savings by utilizing the OES analysis method. In particular, the aforementioned prior art describes a uniform filling of the sample cavity and rapid chilling of the molten metal sample, such that the entire sample section presented for analysis freezes uniformly, and preferably without surface oxidation. The heat content of the solidifying metal is reduced to bring the sampled metal to near room temperature before it is removed from the sampling chamber molds. The obtained samples have smaller volumes than that described in the prior art, so that unnecessary large sample volumes don't preclude rapid solidification of the molten metal sample.

Hence, the samples described in EP3336513A1, EP3336514A1, EP3336512A1, and EP3336511A1 can be analyzed by Spark-OES without surface preparation and thereby potential economic benefit is gained.

DA samplers used for high oxygen applications, such as in a converter process, an Electric Arc Furnace, EAF, process, or during ladle treatment commonly comprise a de-oxidant material. For example, during ladle treatment the steel is deoxidized by means of aluminum or silicon, depending on the grade requirements. In case high oxygen steel is cooled without the addition of de-oxidants, oxygen will be excreted. This excreted oxygen will recombine with the carbon in the liquid steel, forming CO-bubbles. Such reaction can be fairly violent. In case the steel would freeze, these bubbles will be entrapped in the solidified structure.

Therefore, samplers created for use in high oxygen applications need to contain a de-oxidant material. Often an aluminum material is used as de-oxidant material. However, other materials like a zirconium material, and/or a titanium material can be also employed.

The quantity of de-oxidant material in the sampler is typically in the order of 0.2 to 0.3% of the sample mass. Many different ways of adding the de-oxidant material to the sampler are known, most commonly used is a foil in an inflow conduit of the sampler or a type of rivet at the very end of the inflow conduit. The before described methods of adding a de-oxidant material, for example aluminum, are not suited in combination with a period of argon flushing before the sample is filled. The rivet will melt and dissolve in the steel bath before the filling starts. The use of a foil, often applied as an S-shape uses the friction of the aluminum with the quartz tube as fixation. This friction is not sufficient to withstand the force of the purge while the aluminum weakens from the preheating from the bath. The application of a glue or cement to obtain this fixation will influence the analysis output. Tests have shown that the samples showing very high or very low aluminum content, will also show major deviations in other elements to be analyzed, specifically in carbon.

In standard samples, for example lollypop samples, having a typical sample weight of around 100 g there is much more time available for the de-oxidant material to dissolve and these samples will be grinded to a depth of 0.8 mm to generate a clean homogeneous analysis surface. Even in case that the first entering steel might lose some carbon, this steel will be found in a small corner of the sample at the far end away from the entry point. However, a typical DA sample has a mass between 3 and 10 g and shows a thickness of less than 4 mm, mostly around 2 mm. While the samples are very small, the time available, i.e. the filling time, to obtain a homogeneous distribution of the added de-oxidant material in the sample is very short and a high content of de-oxidant material in a layer at the outer surface of the sample is generally found not acceptable. Contributing to the problem is the fact that most high oxygen applications, more specifically converter applications have a very wide temperature and oxygen range. It is very important to obtain good results at the outer end of this application range. One can consider the total temperature range from around 1550° C. up to 1750° C. and the oxygen range from 100 to 2000 ppm. Even values out of this range can appear, but should be considered exceptional. It should also be mentioned that within this application, the sampling process is done by means of an automatic immersion lance. Due to the variance of the process and the wearing of the lining of the vessel, the immersion depth can vary from about 20 cm up to 1 meter. This variance in immersion depths will generate a lot of variance in the filling speed of the sample. A further problem is the fact that these samples are taken during the processing of the steel with the consequence that analysis values can't be compared to other analysis values.

Therefore, a first objective of the invention is to add the de-oxidant material in a way so that the aforementioned problems are avoided.

Also, the known prior art samplers created for use in low oxygen applications suffer from erroneous measurement results due to carbon and hydrogen components, i.e. hydrocarbons, excreted from the glues and cements used for assembling the sample chamber assembly.

Traditionally, the inflow conduit is mounted in a substantially gas-tight manner to the housing of the sample chamber assembly. When the sampler is submerged in molten metal, the immersion end of the inflow conduit is in contact with the molten metal. The material of the inflow conduit, for example a quartz material, will radiate heat to the sample chamber assembly and preheat the mould being formed by cover plate and housing. Components present at this location will start to decompose. Carbon containing components will start to release carbon containing gases that will condense further in the mould. In addition, once the sample chamber is filled, these components will be formed and condense on the surface of the sample. While the sample is targeted as preparation free sample, this condensation will influence the analysis result and result in erroneous carbon readings.

Therefore, a second objective of the invention is to provide a sampler that provides samples from which precise carbon readings can be taken.

SUMMARY OF THE INVENTION

The invention provides a sampler for taking samples from a molten metal bath, particularly a molten steel bath, the sampler comprising:

a carrier tube having an immersion end;

a sample chamber assembly arranged on the immersion end of the carrier tube, the sample chamber assembly comprising a cover plate and a housing, wherein the housing comprises an immersion end having an opening;

an inflow conduit having a first end for receiving molten metal and a second end, opposite the first end, wherein the second end is in communication with the opening, wherein the opening is configured to receive the molten metal from the inflow conduit;

a measuring head, wherein the sample chamber and the second end of the inflow conduit are at least partly arranged in the measuring head; and a de-oxidant material arranged along a central axis of the inflow conduit, wherein at least part of the de-oxidant material is arranged near the second end of the inflow conduit inside the measuring head, and wherein the inflow conduit comprises first coupling means, arranged on the second end of the inflow conduit, wherein the de-oxidant material comprises second coupling means, to interact with the first coupling means on the inflow conduit to anchor the de-oxidant material in a position along the central axis of the inflow conduit.

Advantageously, before the first entering steel can cool a cavity of the sample chamber formed by the cover plate and housing, the de-oxidant material which is rigidly mounted and held in position, can dissolve in the steel entering the cavity. The de-oxidant material arranged along the central axis in the entry path of the sample chamber is capable to withstand the force of a purging gas while purging, the force of the liquid steel entering the unit during filling, and the de-oxidant material is also capable to dissolve immediately at the very first moment of filling, i.e. since the material is not pushed to a sidewall.

It has been surprisingly found that the configuration according to the invention minimizes the forces of the purge gases during the preheating of the sampler in the molten metal bath and minimizes the preheating of the de-oxidant material from the steel bath, weakening the de-oxidant material. This allows to mount the de-oxidant very close to the immersion end of the measuring head, even at locations that reach 200 to 300° C. during the flushing period. This location can be easily measured in any type of measuring head, it is the preferred mounting/anchoring position.

In one embodiment, the de-oxidant material comprises an aluminum material. Although aluminum has a very low melting point, it is the preferred de-oxidant material because other high melting materials such as zirconium don't melt and need to dissolve in the liquid steel. This is much more time consuming and can't be used over the total application range when used for small DA-type samples. However, other materials like a zirconium material, and/or a titanium material can be also employed.

In another embodiment, the de-oxidant material is shaped as a flat sheet having a thickness of 0.05 to 0.2 mm, more preferably 0.1 to 0.15 mm, most preferred 0.125 mm.

Thicker material will show poor results in low temperature applications, while at high temperature applications the thinner sheet of de-oxidant material will not withstand the force of the incoming steel stream after the preheating.

In yet another embodiment, the amount of de-oxidant material corresponds to 0.1% to 0.5%, preferably 0.2% to 0.3% of the sample mass.

In another embodiment, the inflow conduit comprises a quartz material, preferably a fused quartz material.

In yet another embodiment, the first coupling means is realized by at least one recess, preferably two recesses, in the material of the inflow conduit, arranged towards the second end of the inflow conduit, and wherein the second coupling means is realized by at least one projection, preferably two projections, to interact with the first coupling means on the inflow conduit to anchor the de-oxidant material in the position along the central axis of the inflow conduit.

In an alternative embodiment, the first coupling means is realized by at least one projection, preferably two projections, in the material of the inflow conduit, arranged towards the second end of the inflow conduit, and wherein the second coupling means is realized at least one recess, preferably two recesses, to interact with the first coupling means on the inflow conduit to anchor the de-oxidant material in the position along the central axis of the inflow conduit.

In one embodiment, the de-oxidant material added for the purpose of de-oxidation can be divided in two portions. The first portion that reacts with the oxygen dissolves in the liquid steel and reacts to form alumina (Exothermic reaction), and a second portion that dissolves in the steel microstructure (Endothermic reaction). In case the aluminum is located in a colder area in the inflow conduit the aluminum will have less time and energy available to dissolve in the steel. Poor dissolved aluminum will lead to considerable analysis variances for almost all elements to be analyzed.

In an embodiment, the first and second coupling means are adapted to resist the force of a purge gas to inject the de-oxidant material into the molten metal bath.

The invention also provides a sampler for taking samples from a molten metal bath, particularly a molten steel bath, the sampler comprising:

a carrier tube having an immersion end;

a sample chamber assembly arranged on the immersion end of the carrier tube, the sample chamber assembly comprising a cover plate and a housing, wherein the housing comprises an immersion end having an opening;

an inflow conduit having a first end for receiving molten metal and a second end, opposite the first end, wherein the second end is in communication with the opening, wherein the opening is configured to receive the molten metal from the inflow conduit;

a measuring head, wherein the sample chamber and the second end of the inflow conduit are at least partly arranged in the measuring head; and a metal bushing, wherein the metal bushing coupling the inflow conduit to the sample chamber.

Advantageously, by using a metal bushing for coupling the inflow conduit to the sample chamber no glues or cements are being used for said coupling of the two components. This is because, glues and cements applied on or at the inflow conduit within the measuring head in areas in direct communication with the sample cavity would burn and decompose during the preheating phase of the sampler. Glues and cements applied outside the immersion end of the measuring head would burn or decompose and dissolve in the liquid steel bath during the flushing period in case used in low quantities. Hence, it is preferred that the thickness of the metal bushing is as low as possible, e.g. not exceeding 1 mm for flushing periods of 5 seconds after reaching the deepest immersion point in the liquid steel bath.

Also, the inflow conduit arranged in the metal bushing can be held in place during the immersion process by means of the ferrostatic pressure and liquid steel penetrating in the small gap between the inflow conduit and the metal bushing will freeze. However, a fixation just by friction with the bushing can be sufficient to keep the inlet conduit in place.

An additional benefit of this assembly is its mechanical stability and the ease of production. Another additional benefit of this assembly is an improved fixation of the sample in the mould. After the immersion of the sampler in the bath, the immersion head will fall to the ground and/or the measuring head will be removed to recover the sampler. In both cases the inflow conduit might break. This breaking would reach to the upper end of the inflow conduit in the sample chamber, causing insufficient fixation of the sample in the sample chamber. By moving the end of the inflow conduit towards the immersion end of the measuring head, very good results can be achieved for the fixation of the sample in the sample chamber.

In an embodiment, the metal bushing is adapted to reach from the sample chamber assembly to the first end of the inflow conduit.

Advantageously, the use of a metal bushing that reaches from the sample chamber assembly to the first end, or immersion end of the inflow conduit allows to generate a dry mount, i.e. a mount without the use of glue and/or cement. Such a metal bushing can have a length of around 40 mm, of which about 20 mm are located outside the immersion end of the measuring head.

It is considered very beneficial to apply a metal bushing that will reach to the immersion end of the measuring head. Advantageously, such a metal bushing generates an increased permanent outer diameter around the inlet pin. Due to the flushing period the inflow conduit will be preheated and will not solidify outside the immersion end of the measuring head. After sampling took place, the sampler can be dropped to the shop floor and the sample can be recovered by means of force, i.e. hammering. This force that can be enough for bending a hot inlet pin. The metal bushing prevents the bending of the pin. In case the pin would bend in the direction of the analysis surface of the sample, the sample can't be positioned on the spark-OES instrument without removing the pin, costing a lot of time.

In another embodiment, the metal bushing has at least two different wall thicknesses and/or diameters along its length.

The metal bushing can have different wall-thicknesses and diameters over its length. The wall thickness of the metal bushing outside the measuring head can be minimized and the heat transfer to the sample can be minimized by the application of local reduction in wall-thickness without reducing the desired mechanical strength. Such a metal bushing can be made of several press-fitting parts, or even can be machined from a single piece of metal. Both configurations are considered to fall in the scope of the present invention. One could consider to lower the immersion end of the sampler closer to the immersion end of the measuring head without changing the length of the inflow conduit, however this would generate a high heat flux from the steel-bath to the sampler.

In an embodiment, the metal bushing comprises an aluminum material.

In another embodiment, the inflow conduit comprises a quartz material, preferably a fused quartz material.

In yet another embodiment, the metal bushing having a length of 10 to 40 mm, an inner diameter of 4 mm, and an outer diameter of 6 mm.

In an embodiment, the metal bushing is pressed into the sample chamber for coupling the inflow conduit to the sample chamber.

In another embodiment, the sampler comprising a measuring head supported on the carrier tube and adapted to accommodate at least parts of the sample chamber, and wherein at least part of the metal bushing extends out of the measuring head.

In an embodiment, the sampler comprises a protection cap attached to the first end of the inflow conduit.

In another embodiment, the bushing comprises grooves on an outer surface of the bushing to minimize heat transfer to the sample chamber assembly.

BRIEF DESCRIPTION OF THE DRAWINGS

The following schematic drawings show aspects of the invention for improving the understanding of the invention in connection with some exemplary illustrations, wherein.

DETAILED DESCRIPTION

Figure 1:
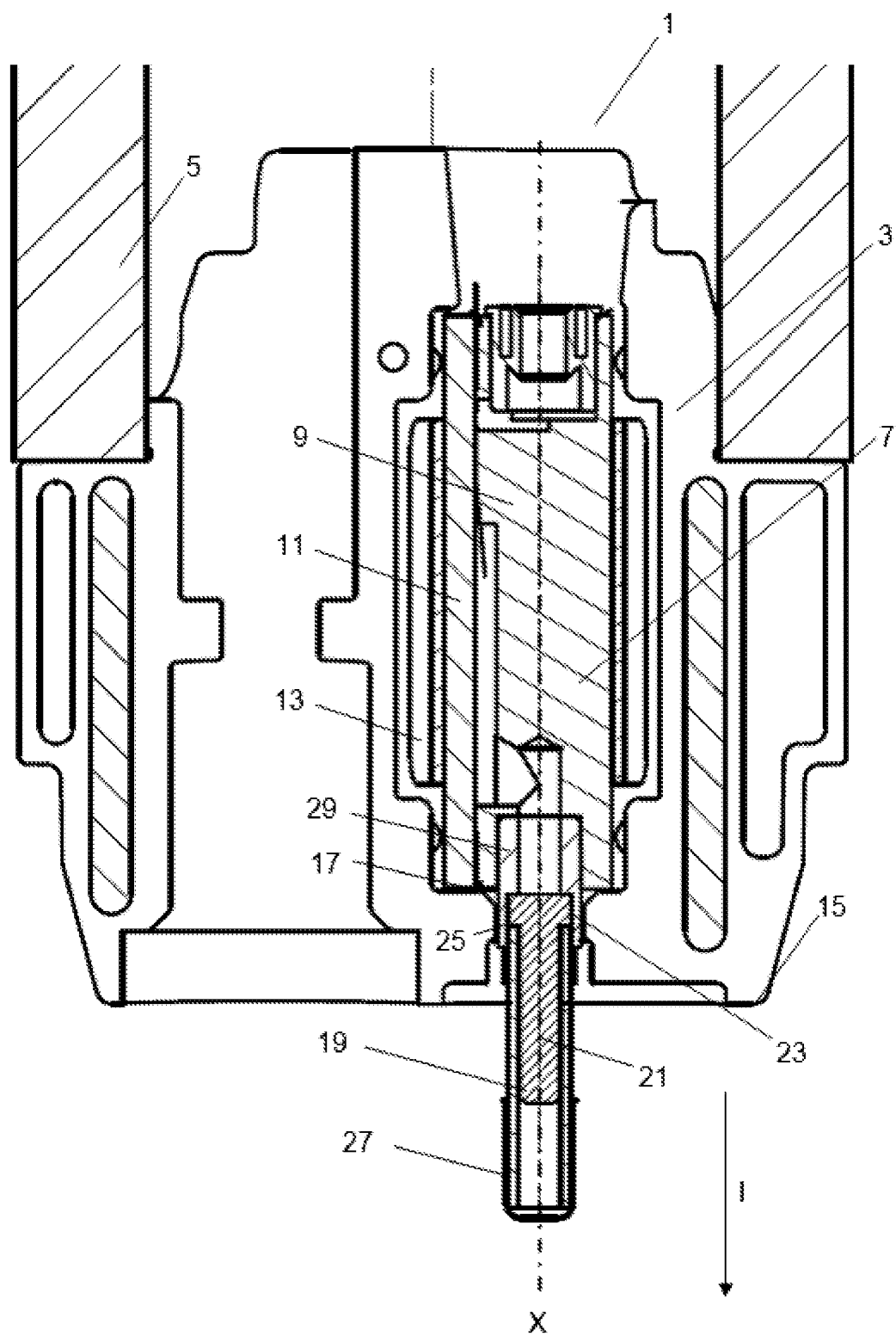
FIGS. 1 and 2 show schematic sectional views of a sampler according to a first embodiment of the invention.
Figure 2:
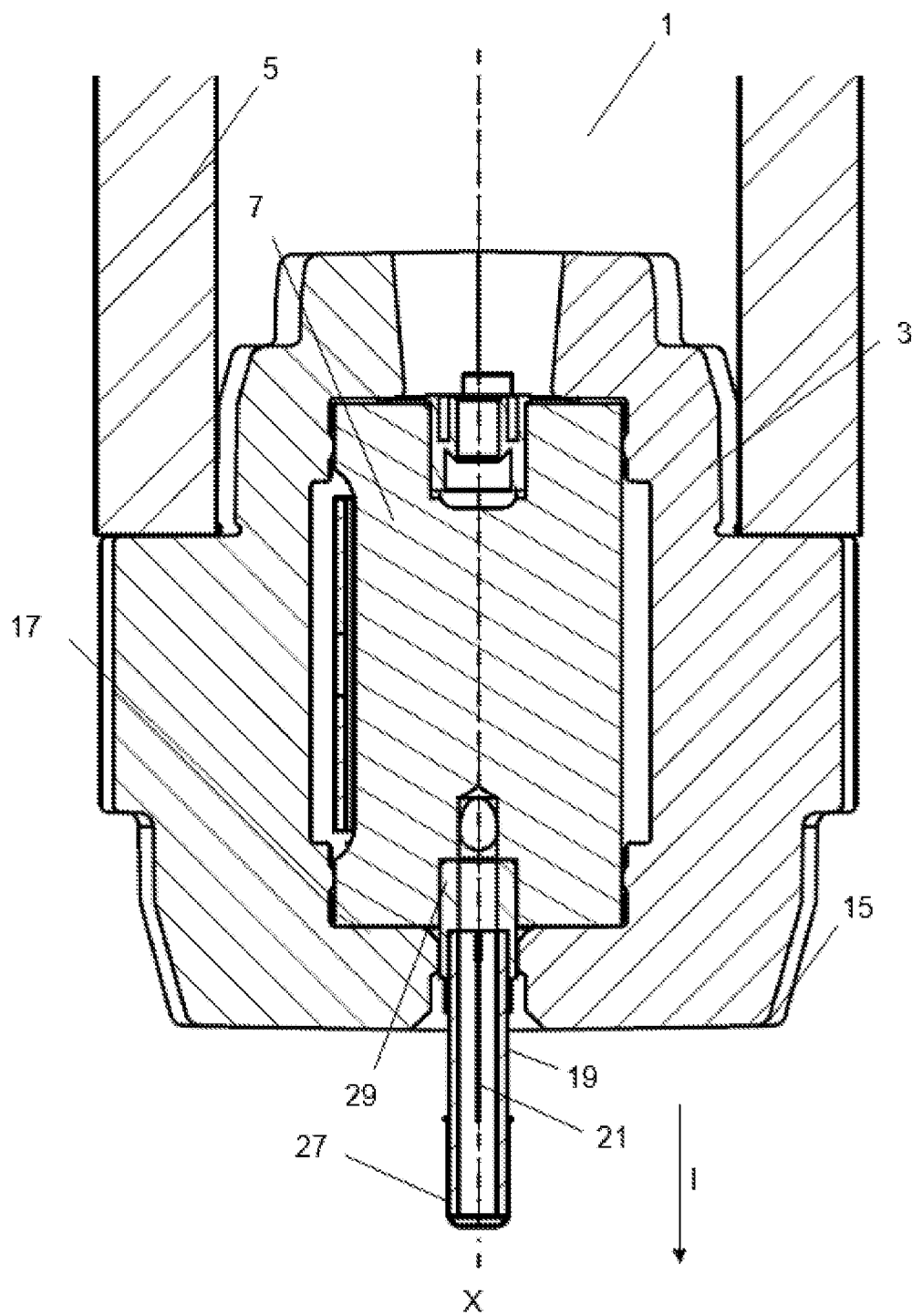

FIGS. 1 and 2 show schematic sectional views of a sampler 1 for taking samples from a molten metal bath according to a first embodiment of the invention. The sampler 1 is suitable for immersion in and sampling of molten steel. The shown sampler 1 comprises a measuring head 3 which can be made of resin bonded silica sand. The measuring head 3 is supported on a carrier tube 5, which can be a paper carrier tube. In use, a probe holder or lance (not shown) is preferably inserted into the interior volume of the carrier tube 5 to provide the mechanical action necessary to submerse the measuring head 3 below the surface of a bath of molten metal (not shown) in the immersion direction I.

The measuring head 3 comprises a sample chamber assembly 7 for collection and retrieval of a sample of molten metal. The sample chamber assembly 7 as shown is a two-part sample chamber composed of a housing 9 and cover plate 11. The housing 9 is preferably formed of one or more materials which are good thermal and electrical conductors, such as, but not limited to, aluminum, copper and other metals having similar thermal and electrical conductivity properties for being electrically coupled to the retrieved metal sample. The housing and the cover plate 9, 11 of the sample chamber assembly 7 can be held together by a clamp 13 with a compression force sufficient to resist a tendency of the two parts 9, 11 of the sample chamber 7 assembly to separate due to the force of molten metal flowing into and filling the sample chamber assembly 7. The clamp 13 can be a metal clamp.

FIGS. 1 and 2 also show the measuring head 3 having a first end and an opposing second end. The first end of the measuring head 5 corresponds to an immersion end 15 of the measuring head 5. The second end of the measuring head 3 is configured to face the lance or probe holder. Also, the sample chamber assembly 7 has a first end and an opposing second end. The first end of the sample chamber assembly 7 corresponds to an immersion end 17 of the sample chamber assembly 7. It will be understood by those skilled in the art that the phrase "immersion end" means the end of the body which is first immersed into molten metal. The first end of the sample chamber assembly 7 is attached to an inflow conduit 19, where the inflow conduit is received at an opening in the housing 9. The inflow conduit 19 enables the flow of molten metal from the molten metal bath into the sample chamber assembly 7. Thus, molten metal is introduced into the sample chamber assembly 7 in the immersion direction I parallel to the central axis X of the sample cavity. The inflow conduit 7 can be made of a quartz material, more preferably a fused quartz material.

FIGS. 1 and 2 also show the de-oxidant material 21 which can be aluminum arranged along the central axis X of the inflow conduit 7. It can also be seen that a part of the de-oxidant material 21 is arranged near the second end of the inflow conduit 19 inside the measuring head 3.

Also shown in FIGS. 1 and 2 are first coupling means 23 at the inflow conduit 19 which can be realized as recesses or protrusions in the material of the inflow conduit 19. The de-oxidant material 21 comprises second coupling means 25 which can be realized as protrusions that interact with the corresponding recesses of the first coupling means 23 or vice versa. Due to the shown coupling means 23, 25 in FIGS. 1 and 2, the de-oxidant material 21 can be reliably hold along the central axis X in the entry path of the sample chamber assembly 9 and is, thus, capable to withstand the force of the purging gas while purging, and the force of the liquid steel entering the unit during the filling.

Also, FIGS. 1 and 2 show a cap 27 arranged at the first end of the inflow conduit 19. When the first end of the inflow conduit is submerged in molten metal, the cap 27 will melt, and molten metal can flow through the inflow conduit 19. Further shown in FIGS. 1 and 2 is a metal bushing 29 that couples the inflow conduit 19 to the housing 9 of sample chamber assembly 7. However, the metal bushing 29 is merely optional for this embodiment. The inflow conduit 19 can be also attached to the housing 9 by means of a glue or a cement.

Figure 3:
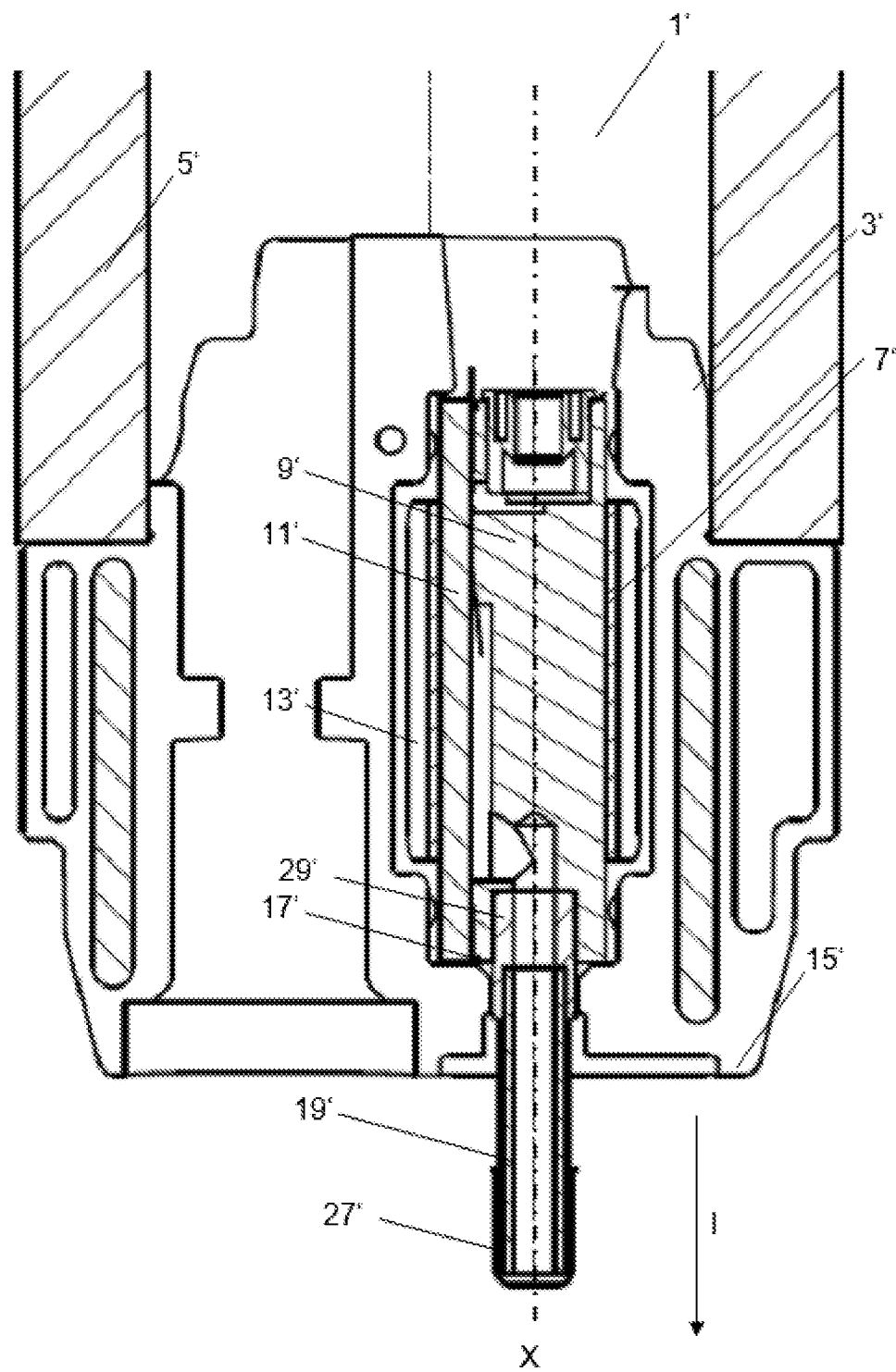
FIGS. 3 and 4 show schematic sectional views of a sampler according to a second embodiment of the invention.
Figure 4:
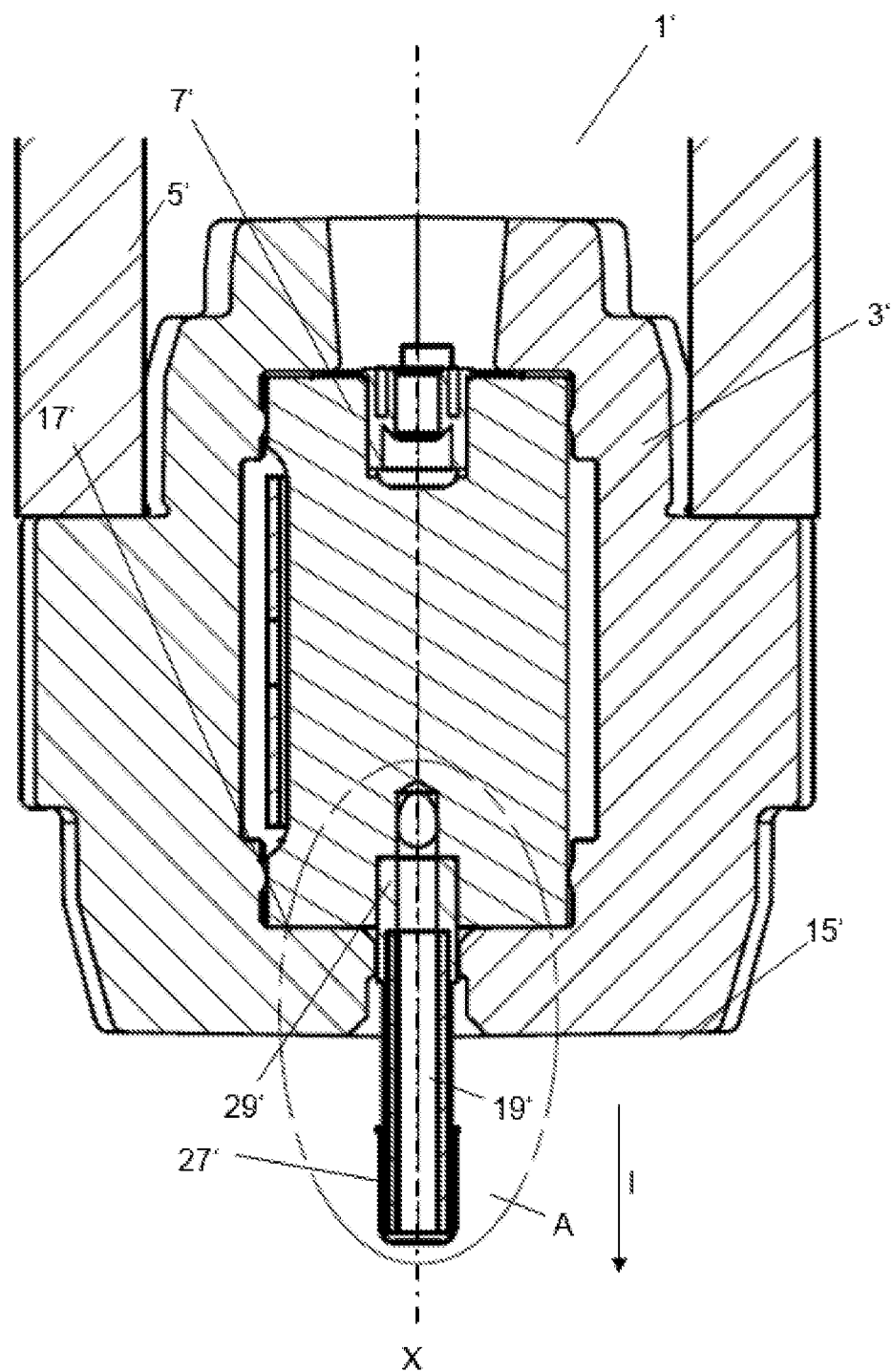

FIGS. 3 and 4 show schematic sectional views of a sampler 1' according to a second embodiment of the invention.

The sampler 1' is suitable for immersion in and sampling of molten steel. The shown sampler 1' comprises a measuring head 3' which can be made of resin bonded silica sand. The measuring head 3' is supported on a carrier tube 5', which can be a paper carrier tube. In use, a probe holder or lance (not shown) is preferably inserted into the interior volume of the carrier tube 5' to provide the mechanical action necessary to submerse the measuring head 3' below the surface of a bath of molten metal (not shown) in the immersion direction I.

The measuring head 3' comprises a sample chamber assembly 7' for collection and retrieval of a sample of molten metal. The sample chamber assembly 7' as shown is a two-part sample chamber composed of a housing 9' and cover plate 11'. The housing 9' is preferably formed of one or more materials which are good thermal and electrical conductors, such as, but not limited to, aluminum, copper and other metals having similar thermal and electrical conductivity properties for being electrically coupled to the retrieved metal sample. The housing and the cover plate 9', 11' of the sample chamber assembly 7' can be held together by a clamp 13' with a compression force sufficient to resist a tendency of the two parts 9', 11' of the sample chamber 7' assembly to separate due to the force of molten metal flowing into and filling the sample chamber assembly 7'. The clamp 13' can be a metal clamp.

FIGS. 3 and 4 also show the measuring head 3' having a first end and an opposing second end. The first end of the measuring head 5' corresponds to an immersion end 15'. The second end of the measuring head 3' is configured to face the lance or probe holder. Also, the sample chamber assembly 7' has a first end and an opposing second end. The first end of the sample chamber assembly 7' corresponds to an immersion end 17'. It will be understood by those skilled in the art that the phrase "immersion end" means the end of the body which is first immersed into molten metal. The first end of the sample chamber assembly 7' is attached to an inflow conduit 19', where the inflow conduit is received at an opening in the housing 9. The inflow conduit 19' enables the flow of molten metal from the molten metal bath into the sample chamber assembly 7. Thus, molten metal is introduced into the sample chamber assembly 7' against the immersion direction I parallel to the longitudinal axis X of the sample cavity. The inflow conduit 7' can be made of a quartz material, more preferably a fused quartz material.

As shown in FIGS. 3 and 4, the sampler 1' also comprises a metal bushing 29' which can comprise an aluminum material. The metal bushing 29' can have a length of 10 to 40 mm, an inner diameter of 4 mm, and an outer diameter of 6 mm. In the shown embodiment, the metal bushing 29' is pressed into the housing 9' of the sample chamber assembly 7' for coupling the inflow conduit 19' to the sample chamber assembly 7'.

Figure 5:
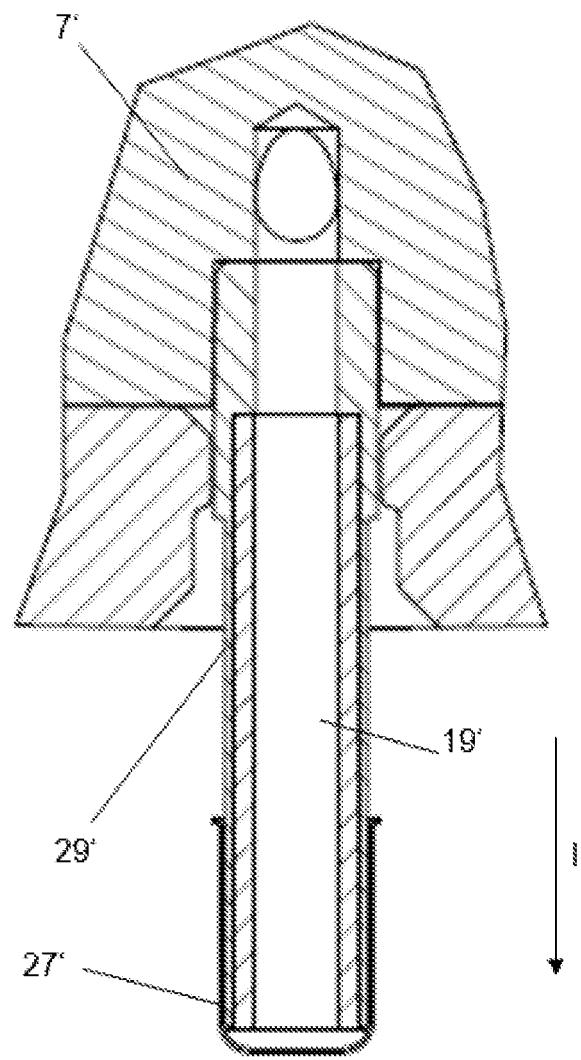
FIG. 5 shows detail 'A' of FIG. 4.

FIG. 5 shows detail 'A' of FIG. 4. As shown, the metal bushing 29' reaches from the sample chamber assembly 7' all the way down to the first end of the inflow conduit 19', and thereby surrounding the inflow conduit 19'. Also, it can be seen that the metal bushing 29' has at least two different wall thicknesses and/or diameters along its length.

Figure 6:
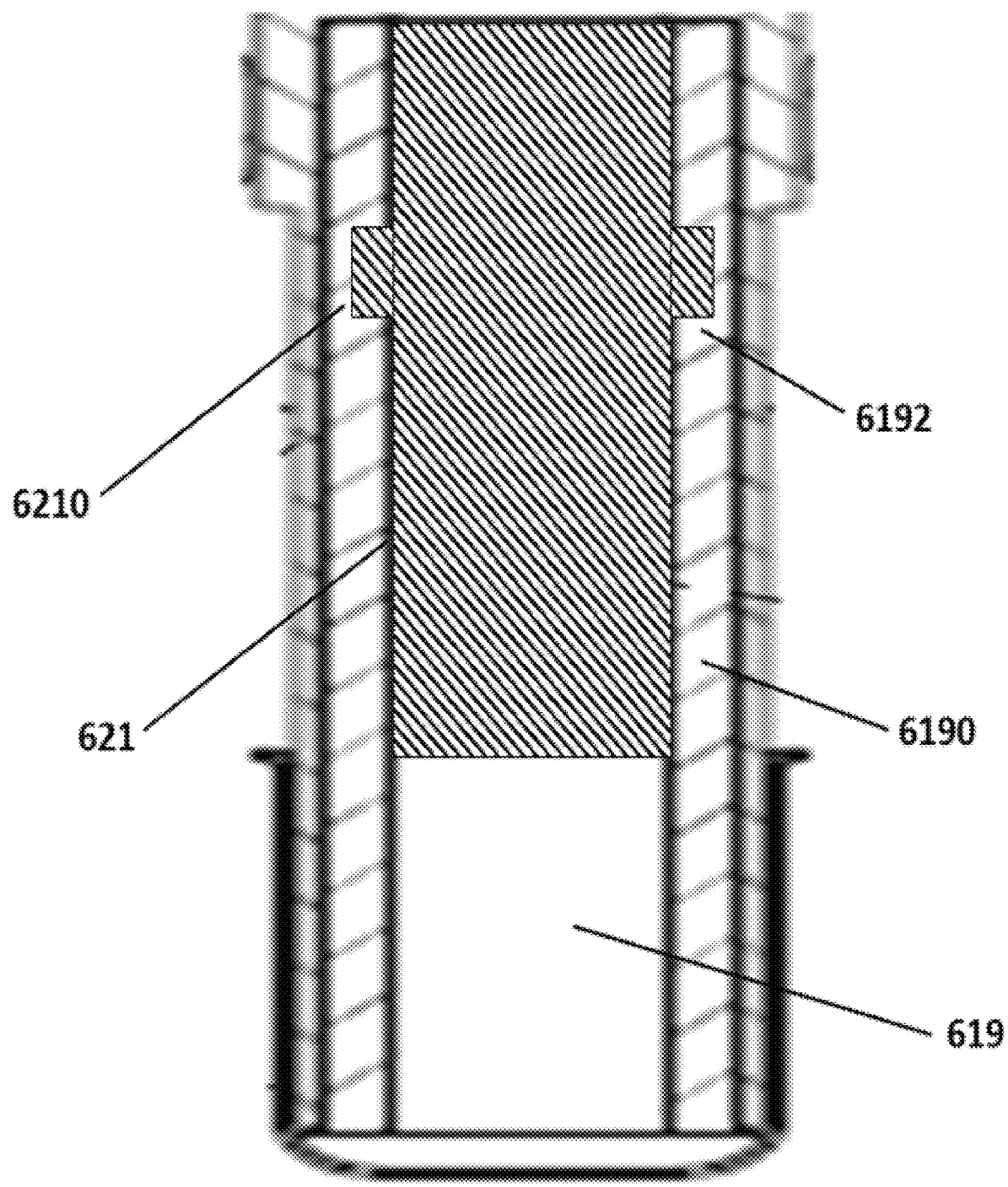
FIG. 6 shows a schematic illustration of an embodiment of the material of the inflow conduit and the de-oxidant material.

In yet another embodiment, the first coupling means is realized by at least one recess, preferably two recesses, in the material of the inflow conduit, arranged towards the second end of the inflow conduit, and wherein the second coupling means is realized by at least one projection, preferably two projections, to interact with the first coupling means on the inflow conduit to anchor the de-oxidant material in the position along the central axis of the inflow conduit. FIG. 6 is a schematic illustration of such an embodiment. As illustrated, the material 6190 of the inflow conduit 619 includes recess 6192 and de-oxidant material 621 includes projection 6210.

Figure 7:
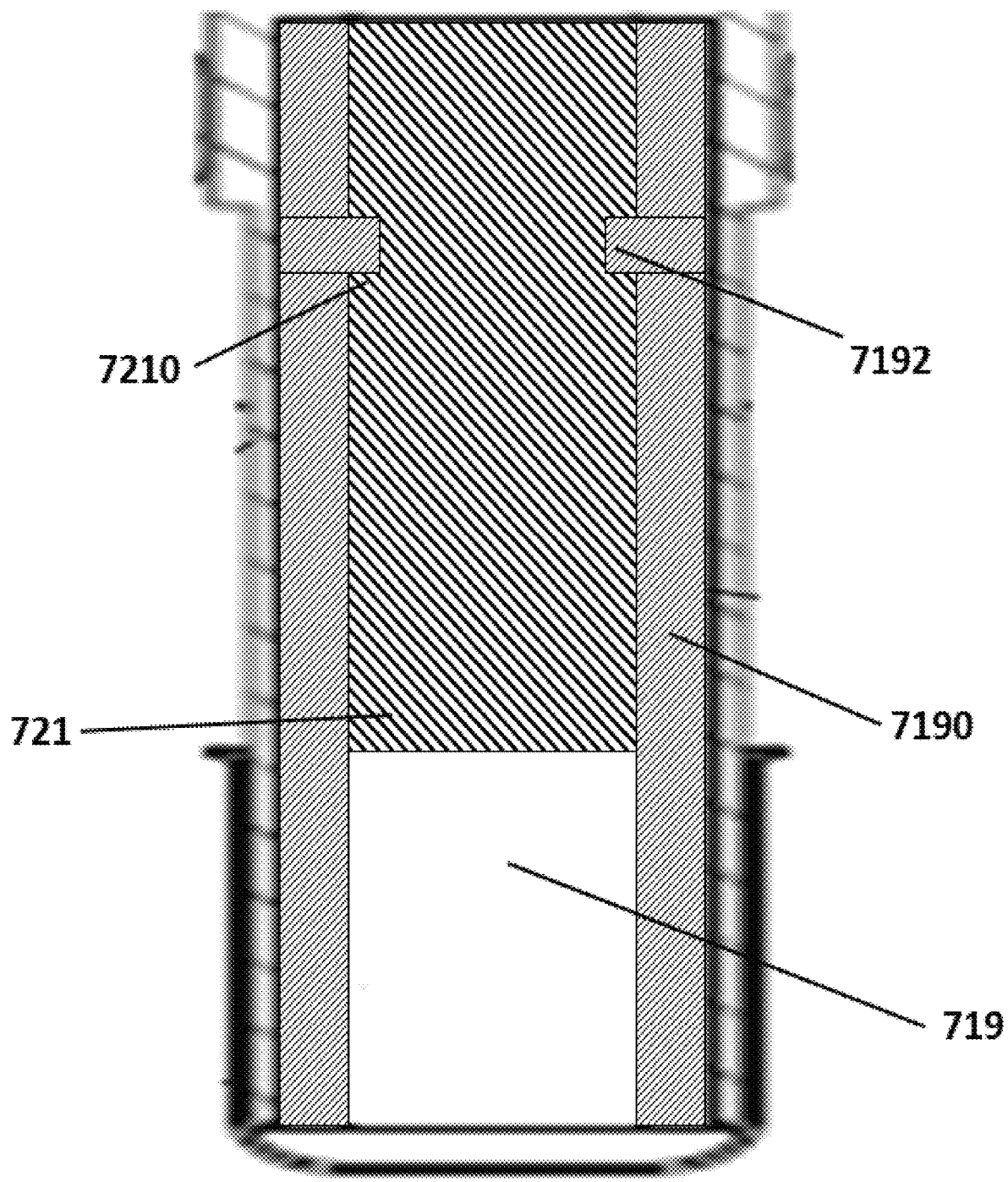
FIG. 7 shows a schematic illustration of another embodiment of the material of the inflow conduit and the de-oxidant material.

In an alternative embodiment, the first coupling means is realized by at least one projection, preferably two projections, in the material of the inflow conduit, arranged towards the second end of the inflow conduit, and wherein the second coupling means is realized at least one recess, preferably two recesses, to interact with the first coupling means on the inflow conduit to anchor the de-oxidant material in the position along the central axis of the inflow conduit. FIG. 7 is a schematic illustration of such an embodiment. As illustrated, the material 7190 of the inflow conduit 719 includes protrusion 7192 and de-oxidant material 721 includes recess 7210.

The features disclosed in the claims, the specification, and the drawings maybe essential for different embodiments of the claimed invention, both separately or in any combination with each other.

REFERENCE SIGNS 1, 1' Sampler
3, 3' Measuring Head
5. 5' Carrier Tube
7, 7' Sample Chamber Assembly
9, 9' Housing
11, 11' Cover Plate
13, 13' Clamp
15, 15' Immersion End of Measuring Head
17, 17' Immersion End of Sample Chamber
19, 19' Inflow Conduit
21 De-Oxidant Material
23 First Coupling Means
25 Second Coupling Means
27, 27' Cap
29, 29' Metal Bushing
A Detail
I Immersion Direction
X Central Axis

The invention claimed is:
1. A sampler for taking samples from a molten metal bath, the sampler comprising:
a carrier tube having an immersion end;
a sample chamber assembly arranged on the immersion end of the carrier tube, the sample chamber assembly comprising a cover plate and a housing, wherein the housing comprises an immersion end having an opening;
an inflow conduit having a first end for receiving a molten metal sample and a second end, opposite the first end, wherein the second end is in communication with the opening, wherein the opening is configured to receive the molten metal sample from the inflow conduit;
a sampler head, wherein the sample chamber assembly and the second end of the inflow conduit are at least partly arranged in the sampler head; and
a de-oxidant material anchored in a position and arranged along a central axis of the inflow conduit, wherein at least part of the de-oxidant material is arranged near the second end of the inflow conduit inside the sampler head, and wherein the de-oxidant material comprises at least one protrusion and a material of the inflow conduit comprises at least one recess, the at least one protrusion engaging the at least one recess to anchor the de-oxidant material, or wherein the de-oxidant material comprises at least one recess and the material of the inflow conduit comprises at least one projection, the at least one protrusion engaging the at least one recess to anchor the de-oxidant material.

2. The sampler of claim 1, wherein the de-oxidant material comprises an aluminum material.

3. The sampler of claim 1, wherein the de-oxidant material is shaped as a flat sheet having a thickness of 0.05 to 0.2 mm.

4. The sampler of claim 1, wherein the amount of the de-oxidant material ranges from to 0.1% to 0.5% of the mass of the molten metal sample to be sampled from the molten metal bath.

5. The sampler of claim 1, wherein the inflow conduit comprises a quartz material.

6. The sampler of claim 5, wherein the quartz material is a fused quartz material.

7. The sampler of claim 1, wherein the molten metal sample is a molten steel.

8. The sampler of claim 1, wherein the de-oxidant material is shaped as a flat sheet having a thickness of 0.1 to 0.15 mm.

9. The sampler of claim 1, wherein the amount of the de-oxidant material ranges from to 0.2% to 0.3% of the mass of the molten metal sample to be sampled from the molten metal bath.

10. The sampler of claim 1, wherein the de-oxidant material comprises at least one of a zirconium material and a titanium material.

11. The sample of claim 1, wherein the housing and the flat cover plate are held together with a clamp.

* * * * *

UNITED STATES PATENT AND TRADEMARK OFFICE
CERTIFICATE OF CORRECTION

| | | |
|---|---|---|
| PATENT NO. | : 11,592,363 B2 | Page 1 of 1 |
| APPLICATION NO. | : 16/434901 | |
| DATED | : February 28, 2023 | |
| INVENTOR(S) | : Jan Doets et al. | |

It is certified that error appears in the above-identified patent and that said Letters Patent is hereby corrected as shown below:

On the Title Page

(30) Foreign Application Priority Data
Change:
"Jun. 12, 2018 (EP) ............................ 18177317"
To:
--Jun. 12, 2018 (EP) ............................ 18177317.7--

Signed and Sealed this
Fourth Day of April, 2023

Katherine Kelly Vidal
*Director of the United States Patent and Trademark Office*